(12) United States Patent  (10) Patent No.: US 9,700,377 B2
Kwon  (45) Date of Patent: Jul. 11, 2017

(54) SURGICAL ROBOT FOR CHANGING POSITION OF SURGICAL EQUIPMENT

(71) Applicants: KOHYOUNG TECHNOLOGY INC., Seoul (KR); INDUSTRY-UNIVERSITY COOPERATION FOUNDATION HANYANG UNIVERSITY ERICA CAMPUS, Ansan-si Gyeonggi-do (KR)

(72) Inventor: YoungSik Kwon, Ansan-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-si, Gyeonggi-Do (KR)

( * ) Notice: Subject to any disclaimer, the term of this patent is extended or adjusted under 35 U.S.C. 154(b) by 257 days.

(21) Appl. No.: 14/005,071

(22) PCT Filed: Apr. 17, 2013

(86) PCT No.: PCT/KR2013/003250
§ 371 (c)(1),
(2) Date: Sep. 13, 2013

(87) PCT Pub. No.: WO2013/162205
PCT Pub. Date: Oct. 31, 2013

(65) Prior Publication Data
US 2015/0088160 A1  Mar. 26, 2015

(30) Foreign Application Priority Data

Apr. 27, 2012 (KR) .......................... 10-2012-0044935

(51) Int. Cl.
*A61B 19/00* (2006.01)
*A61B 34/30* (2016.01)

(52) U.S. Cl.
CPC .......... *A61B 19/2203* (2013.01); *A61B 34/30* (2016.02); *A61B 2034/301* (2016.02)

(58) Field of Classification Search
CPC .......... A61B 19/2203; A61B 2034/301; A61B 2034/302; A61B 2034/303;
(Continued)

(56) References Cited

U.S. PATENT DOCUMENTS

2003/0135204 A1* 7/2003 Lee ........................ A61B 34/20
606/1
2009/0137952 A1* 5/2009 Ramamurthy ........... A61B 5/06
604/95.01
(Continued)

FOREIGN PATENT DOCUMENTS

JP  2002-159499  6/2002
JP  2006-518261  8/2006
(Continued)

OTHER PUBLICATIONS

International Search Report for International Application No. PCT/KR2013/003250, dated Jul. 25, 2013.

*Primary Examiner* — Melanie Tyson
*Assistant Examiner* — Erich Herbermann
(74) *Attorney, Agent, or Firm* — Kile Park Reed & Houtteman PLLC

(57) ABSTRACT

Provided is a surgical robot for changing a position of surgical equipment capable of selectively using the surgical equipment appropriate for affected areas by rotating the surgical equipment instead of changing a position of the surgical equipment by detachment, by integrating a plurality of flexible shafts having a surgical equipment attached to a (Continued)

leading end thereof to configure a single shaft assembly and allowing each flexible shaft to perform translation, rotation, and bending motions and rotating the shaft assembly. According to the embodiment of the present invention, the surgical robot for changing a position of surgical equipment includes: a housing 200 coupled with a rear end of the frame fixing part 100; a curved frame 300 coupled with a leading end of the frame fixing part 100; and a shaft assembly 400, wherein the shaft assembly 400 penetrates through the curved frame 300 within the housing 200 to be exposed to a leading end of the curved frame 300 and rotates within the curved frame 300.

12 Claims, 7 Drawing Sheets

(58) Field of Classification Search
CPC ........ A61B 2034/305; A61B 2034/306; A61B 2034/715; A61B 34/30; A61B 34/70; A61B 34/71; A61B 2019/26; A61B 17/3421
USPC ................. 606/130, 204–206; 600/104–106; 74/490.05, 490.01; 623/23.16, 24; 318/568.11, 568.21
See application file for complete search history.

(56) References Cited

U.S. PATENT DOCUMENTS

| | | | |
|---|---|---|---|
| 2010/0036198 A1* | 2/2010 | Tacchino | A61B 1/0014 600/106 |
| 2010/0217072 A1* | 8/2010 | Kondoh | A61B 1/00071 600/101 |
| 2010/0274087 A1* | 10/2010 | Diolaiti | A61B 1/00087 600/118 |
| 2011/0118543 A1* | 5/2011 | Dosher | A61B 17/3421 600/104 |

FOREIGN PATENT DOCUMENTS

| | | |
|---|---|---|
| JP | 2008-220972 | 9/2008 |
| KR | 10-2011-0120476 | 11/2011 |
| KR | 10-2011-0126260 | 11/2011 |
| WO | 2004073527 | 9/2004 |

* cited by examiner (a)

(b)

SURGICAL ROBOT FOR CHANGING POSITION OF SURGICAL EQUIPMENT

TECHNICAL FIELD

The present invention relates to a surgical robot for changing a position of surgical equipment, and more particularly, to a surgical robot for changing a position of surgical equipment capable of selectively using the surgical equipment appropriate for affected areas by rotating the surgical equipment instead of changing a position of the surgical equipment by detachment, by integrating a plurality of flexible shafts having a surgical equipment attached to a leading end thereof to configure a single shaft assembly and allowing each flexible shaft to perform translation, rotation, and bending motions and rotating the shaft assembly.

BACKGROUND ART

As illustrated in FIG. 11, a surgical robot (for example, da Vinci Surgical System of Intuitive Surgical, Inc.) according to the related art used for a laparoscope has a structure in which each robot arm 710 is present and a leading end of the robot arm is attached with a surgical equipment 720 (end-effector).

Since an abdominal cavity has a wide affected area and a sufficient operation space, as illustrated, each robot arm 710 is configured in a straight type and a body 700 supports each robot arm 710 to control a direction and an advance and retreat of the robot arm and since the positions of the surgical equipments are changed by extracting the robot arms 710 from the abdominal cavity and then detaching and attaching the surgical equipments 720 mounted at ends of the robot arms at the time of changing the positions of the surgical equipments 720 mounted at the ends of the robot arms, there is no need to change the positions of the surgical equipments within the abdominal cavity.

However, the surgical robot is easily applied to wide affected areas such as abdominal cavity, but may not be easily applied to narrow affected areas. For example, since an occipital region has only a size of approximately 25 mm×25 mm even in the case of an adult, an oral cavity which is a passage through which the surgical equipment enters the occipital region has a limited size, and the occipital region is disposed at an inwardly bent place, it is difficult to perform a surgery only by the miniaturization of the surgical robot having the straight robot arm according to the related art.

Further, since at least two surgical equipments and three to four surgical equipments for a smooth use are inserted into a narrow space of the occipital region, every time the position of the surgical equipment is changed, an operation of extracting and inserting these surgical equipments may be very cumbersome.

DISCLOSURE

Technical Problem

An object of the present invention is to provide a surgical robot for changing a position of surgical equipment capable of using a plurality of surgical equipments appropriate for affected areas without detaching the surgical equipments by integrating the surgical equipments and changing positions of each surgical equipment by rotation.

Technical Solution

In one general aspect, there is provided a surgical robot for changing a position of surgical equipment, including: a frame fixing part 100; a housing 200 coupled with a rear end of the frame fixing part 100; a curved frame 300 coupled with a leading end of the frame fixing part 100; and a shaft assembly 400, wherein the shaft assembly 400 penetrates through the curved frame 300 within the housing 200 to be exposed to a leading end of the curved frame 300 and rotates within the curved frame 300.

The housing 200 may be configured to include a housing rear end 220 and a housing front end 210 coupled with the shaft assembly 400 and the housing front end 210 may rotate with respect to the housing rear end 220.

A leading end of the housing 200 may be provided with a rotating plate 211 rotating by a rotating driving part 240 and the rotating plate 211 may be coupled with a shaft holder 230 into which the flexible shaft 410 is inserted.

The shaft holder 230 may be detachably coupled with a moving member 216 within the housing 200 to advance and retreat the flexible shaft 410 and each surface on which the shaft holder 230 and the moving member 216 are coupled with each other may be formed with power terminals POW and control terminals CON.

The curved frame 300 may be configured to include a fixed frame 310 coupled with the leading end of the frame fixing part 100 and a rotating frame 320 rotatably mounted at the leading end of the fixed frame 310 and the rotating frame 320 may be coupled with a fixture configured to include a fixed plate 322 and a tension wire 323 pulling the fixed plate.

Advantageous Effects

As set forth above, according to the surgical robot for changing a position of surgical equipment according to the embodiments of the present invention, the surgical equipments appropriate for affected areas can be used by appropriately changing the positions of the surgical equipments only by the rotation of the integrated surgical equipments without detaching the surgical equipments in the state in which the integrated surgical equipments enter an occipital region, a vagina, a rectum, and the like.

DESCRIPTION OF DRAWINGS

The above and other objects, features and advantages of the present invention will become apparent from the following description of preferred embodiments given in conjunction with the accompanying drawings, in which.

BEST MODE

Figure 1:
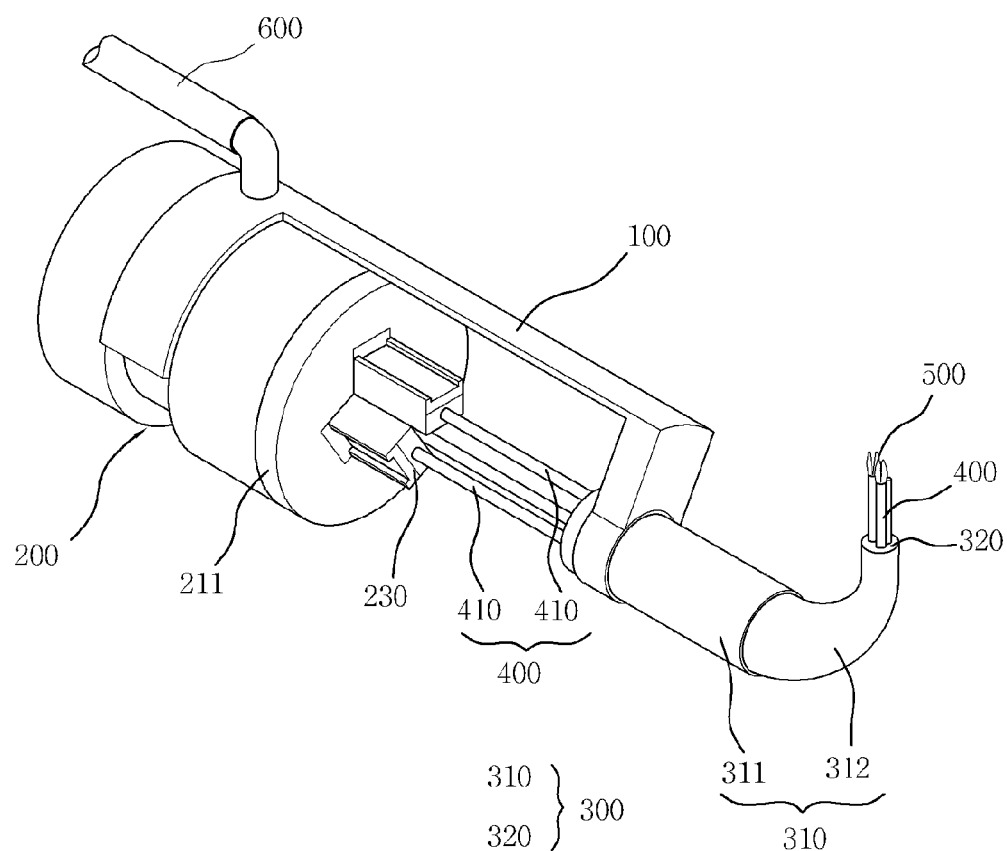
FIG. 1 is a perspective view of a surgical robot for changing a position of surgical equipment according to an embodiment of the present invention.

FIG. 1 is a perspective view of a surgical robot for changing a position of surgical equipment according to an embodiment of the present invention.

The surgical robot for changing a position of surgical equipment according to an embodiment of the present invention has a frame fixing part 100 and a position of surgical equipment 500 exposed to a leading end of a curved frame 300 is changed by coupling a housing 200 with the frame fixing part 100 and rotating a shaft assembly 400 which is a set of flexible shafts 410 protruding to one side of the housing 200.

In general, to perform a surgery, forceps gripping a surgical site and scissors cutting the gripped site are basically required. Therefore, the surgical robot for changing a position of surgical equipment according to an embodiment of the present invention includes a flexible shaft having forceps mounted at a leading end thereof and a flexible shaft mounted at a leading end thereof and for convenience of surgery, may include a flexible shaft having accessory devices, such as an endoscope, a lighting device, a knife, a snare, and a coagulator, mounted at a leading end thereof.

The flexible shaft 410 may be configured to independently perform a translation motion, a rotation motion, a bending motion and may be independently controlled (for example, the flexible shaft and the operation driving part thereof are generally configured to embed a plurality of wires in an outer circumferential edge of one flexible shaft along a longitudinal direction thereof at a uniform interval and control the rotation and bending motions of the corresponding shaft by controlling the wires and the detailed description thereof will be omitted). An operator may bend, for example, one flexible shaft while advancing the one flexible shaft, rotate another flexible shaft while retreating the flexible shaft, and bend while rotating another flexible shaft.

Each component of the surgical robot for changing a position of surgical equipment according to the embodiment of the present invention will be described below in detail.

The frame fixing part 100 has the housing 200 coupled with a rear end thereof and the curved frame 300 coupled at a leading end thereof to support the overall structure of the surgical robot for changing a position of surgical equipment according to the embodiment of the present invention. The frame fixing part 100 is coupled with a holding member 600 which is gripped by an operator or mounted on a mounting table and the holding member 600 rotates the shaft assembly 400 by using electricity while supporting the frame fixing part 100 or becomes a passage transferring power and a signal for driving and controlling the surgical equipment 500.

The housing 200 includes a rotating plate 211, from which a shaft holder 230 protrudes, mounted at a leading end thereof and the shaft holder 230 may rotate by allow a rotating driving part 240 to rotate the rotating plate 211 using electricity and an operator may rotate the shaft holder 230 by manually rotating a portion of the housing 200.

Figure 2:
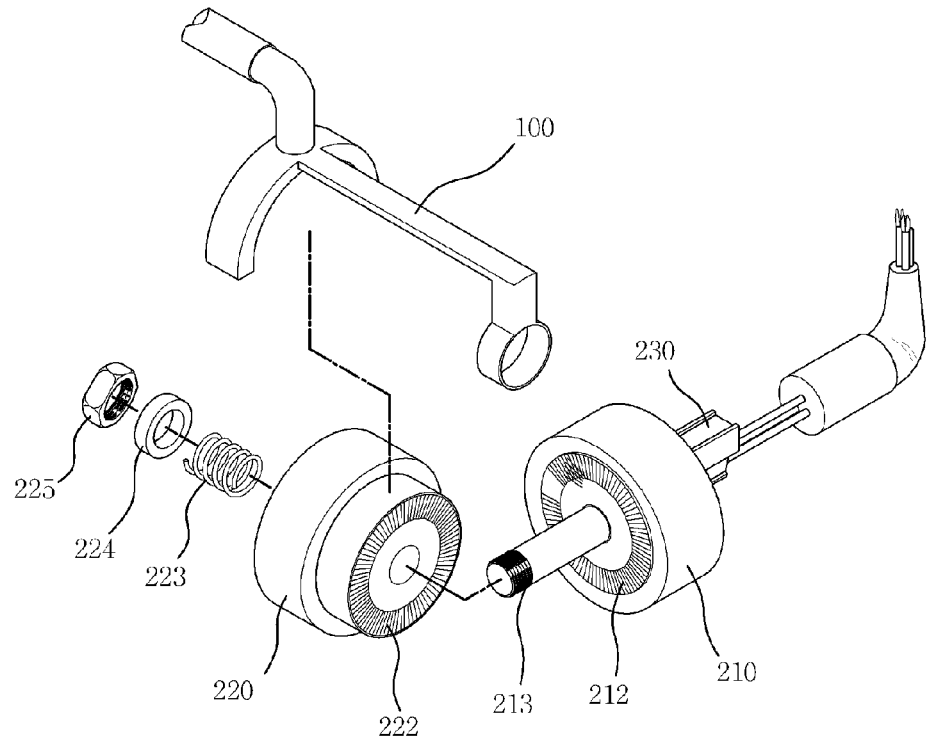
FIG. 2 is an exploded view of one embodiment of a housing illustrated in FIG. 1.

FIG. 2 is an exploded view of one embodiment of the housing 200 of FIG. 1. Referring to FIG. 2, the housing 200 is configured to include a housing front end 210 from which the shaft holder 230 protrudes and a housing rear end 220 elastically coupled with the housing front end 210 and surfaces on which the housing front end 210 and the housing rear end 220 are coupled with each other are each formed with saw-toothed projections 212 and 222 in a cylindrical shape. Further, a screw shaft 213 protruding from the housing front end 210 penetrates through the housing rear end 220 to be coupled with a spring 223, a washer 224, and a nut 225, such that the housing rear end 220 is elastically adhered to the housing front end 210. By the above structure, when an operator rotates the housing front end 210, the housing front end 210 rotates in the state in which it is elastically adhered to the housing rear end 220 and after the rotation of the housing front end is completed, the position of the housing front end 210 is fixed by the saw-toothed projections 212 and 222 formed on the housing front end 210 and the housing rear end 220.

Figure 3:
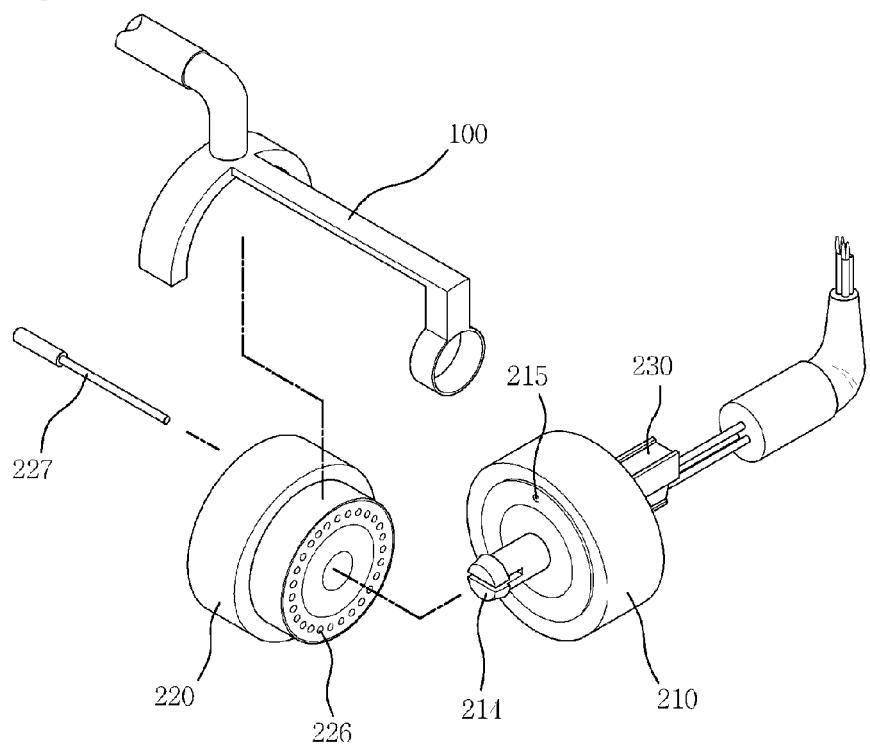
FIG. 3 is an exploded view of another embodiment of the housing of FIG. 1.

FIG. 3 is an exploded view of another embodiment of the housing 200 of FIG. 1. Referring to FIG. 3, the housing 200 is configured to include the housing front end 210 from which the shaft holder 230 protrudes and the housing rear end 220 coupled with the housing front end 210 by a coupling member 214 and the housing front end 210 is formed with a fixing hole 215 and the housing rear end 220 is formed with a plurality of through holes 226 in a cylindrical shape. By the above structure, after an operator rotates the housing front end 210, a fixing pin 227 is coupled with the fixing hole 215 by penetrating through any one of the plurality of through holes 226, such that a relative position of the housing front end 210 and the housing rear end 220 is fixed.

Figure 4:
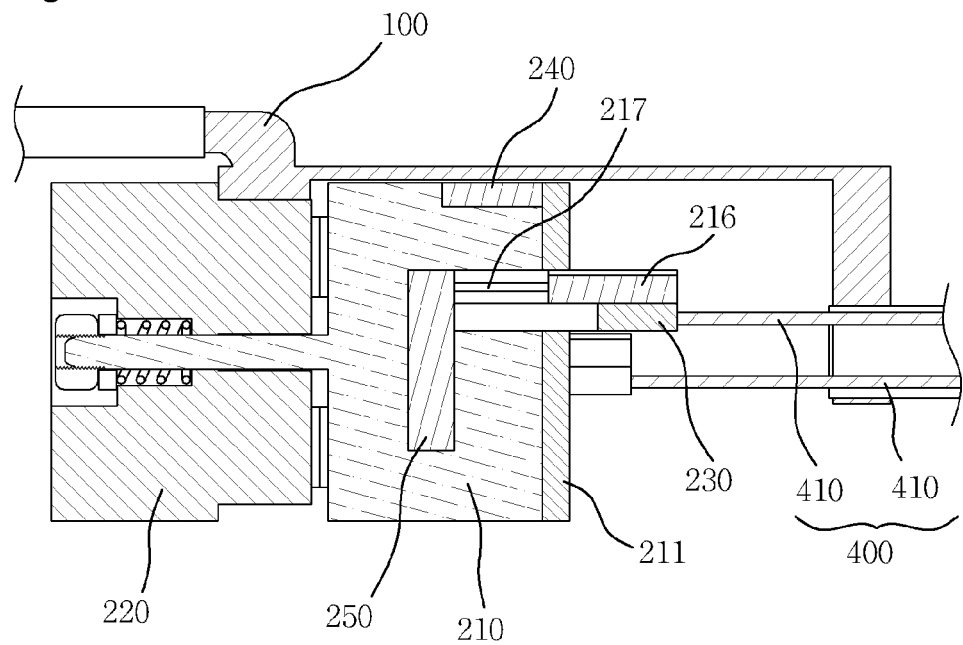
FIG. 4 is a cross-sectional view of the housing of FIG. 2.

FIG. 4 is a cross-sectional view of the housing 200 of FIG. 2. Referring to FIG. 4, the shaft holder 230 protruding to one side of the housing front end 210 is inserted with the flexible shaft 410 and when the rotating plate 211 rotates by the rotating driving part 240 embedded in the housing 200, the shaft holder 230 and the flexible shaft 410 may integrally rotate with the rotating plate 211 and the shaft holder 230 is coupled with the moving member 216 within the housing front end 210 to advance and retreat the moving member 216 so as to advance and retreat the flexible shaft 410 and the moving member 216 is driven by a straight moving member 217 such as a straight motor or a ball screw.

Further, the housing 200 has an operation driving part 250 driving the flexible shaft 410 embedded therein to be mounted to integrally rotate with the flexible shaft 410. As such, when the operation driving part 250 and the flexible shaft 410 rotate integrally, even though the flexible shaft 410 rotates, the relative position between each flexible shaft 410 and the operation driving part 250 may be fixed to prevent a power line or a control line from being twisted and simplify the structure.

The flexible shaft 410 is disposed to be spaced apart from a rotating center of the shaft assembly 400 by a predetermined distance so that the flexible shaft 410 may be appropriately changed by rotation. Herein, both of a distance between each flexible shaft 410 and the rotating center of the shaft assembly 400 and a distance between the respective shaft holders 230 do not need to be uniform and these distances may be appropriately set in consideration of the overall conditions, such as the disposition of the surgical equipment 500 attached to the leading end of the flexible shaft 410. The flexible shaft 410 inserted into the shaft holder 230 penetrates through the curved frame 300 to be described below.

Figure 5:
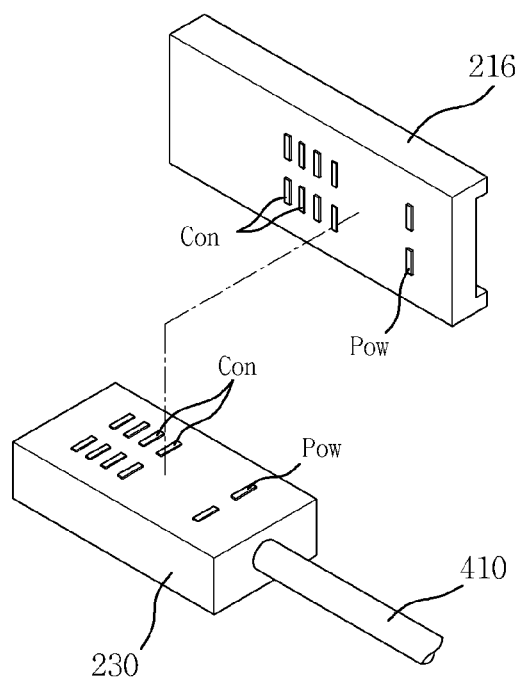
FIG. 5 is a diagram illustrating a coupled structure of a shaft holder and a moving member.

FIG. 5 illustrates a structure in which the shaft holder 230 according to the embodiment of the present invention is detachably coupled with the moving member 216 within the housing 200. Each surface on which the shaft holder 230 and the moving member 216 are coupled with each other is formed with power terminals POW and control terminals CON so as to transfer the power and control signal by a contact. By the above structure, an operator may combine the surgical equipments 500 appropriate for a surgery only by a simple operation of replacing the shaft holder 230.

Figure 6:
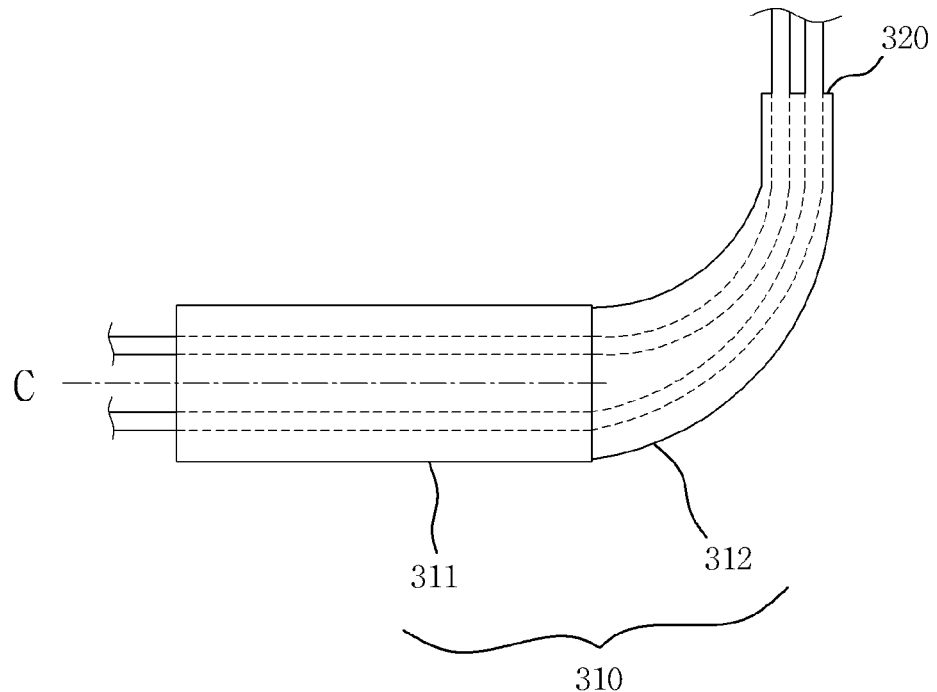
FIG. 6 is a cross-sectional view of a curved frame of FIG. 1.

FIG. 6 is a cross-sectional view of the curved frame 300 of FIG. 1.

Referring to FIGS. 1 and 6, since the curved frame 300 of the surgical robot for changing a position of surgical equipment according to the embodiment of the present invention is fixed to the frame fixing part 100 together with the housing 200, the relative position with respect to the housing 200 is not changed.

The curved frame 300 includes a fixed frame 310 mounted at the leading end of the frame fixing part 100 and a rotating frame 320 rotatably mounted at the leading end of the fixed frame 310. The fixed frame 310, which is a rigid body, maintains the shape in the state in which it is fixed to the frame fixing part 100. Therefore, even though the flexible shaft 410 rotates by the rotation of the rotating plate 211, the fixed frame 310 maintains the shape, while being fixed.

The fixed frame 310 is configured to include a straight part 311 fixed to the frame fixing part 100 and a curved part 312 which is connected to a leading end of the straight part 311 and may reach the occipital region through a patient's oral cavity.

The rotating frame 320 is rotatably mounted at the end of the fixed frame 310 and may minimize friction force using a bearing, and the like.

The rotating frame 320 is formed with a channel through which the plurality of flexible shafts 410 each penetrate to be able to be slid.

Figure 7:
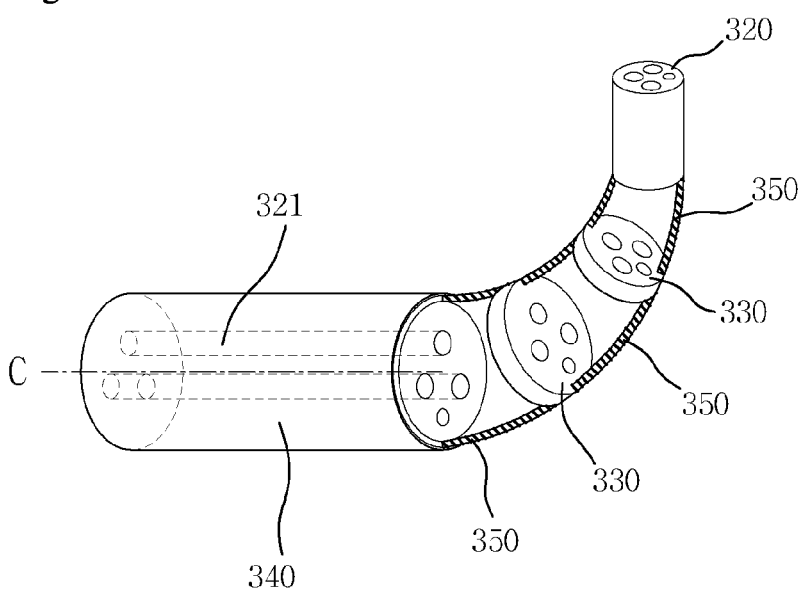
FIG. 7 is a perspective view illustrating an inside of the curved frame of FIG. 6.

FIG. 7 is a perspective view illustrating an inside of the curved frame 300 of FIG. 6. Referring to FIG. 7, the straight part 311 of the fixed frame 310 is formed with a channel 321 through which the flexible shaft 410 penetrates to be able to be slid and is provided with a spacer 340 rotating with respect to a rotating center C. When the plurality of flexible shafts 410 rotate integrally, the spacer 340 rotates together while maintaining the interval, such that the rotating force of the flexible shaft 410 transferred from the rotating driving part 240 is transferred up to the rotating frame 320.

Further, the curved part 312 of the fixed frame has one or more than two rotating links 330 embedded therein, if necessary, in which the rotating links 330 are formed with through holes through which the plurality of flexible shafts 410 each penetrate to be able to be slid, and each rotating link 330 also rotates together with the flexible shaft 410.

Herein, the rotating frame 320, the rotating link 330, and the spacer 340 may be connected to each other by a member 350 which may be elastically deformed in a longitudinal direction.

Figure 8:
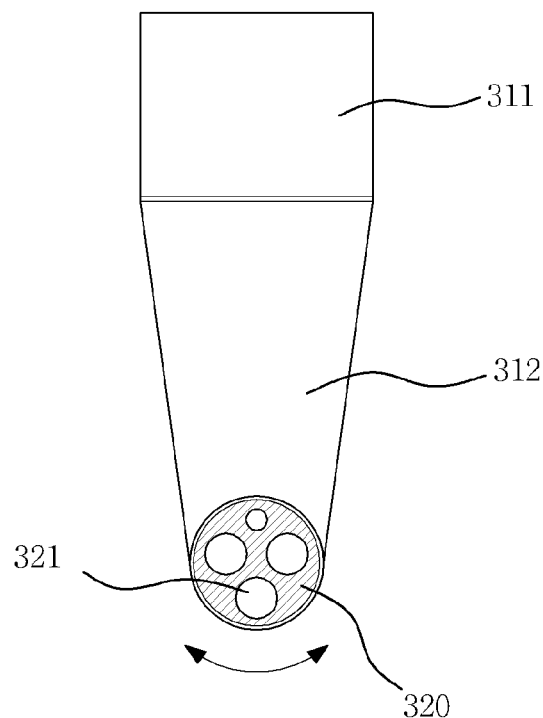
FIG. 8 is a front view of the curved frame of FIG. 6.

FIG. 8 is a front view of the curved frame 300 of FIG. 6. The position of the flexible shaft 410 protruding by penetrating through the channel 321 by the rotation of the rotating frame 320 mounted at the leading end of the curved frame 300 may be changed and the surgical equipment 500 attached to the flexible shaft 410 may move to a desired position.

Figure 9:
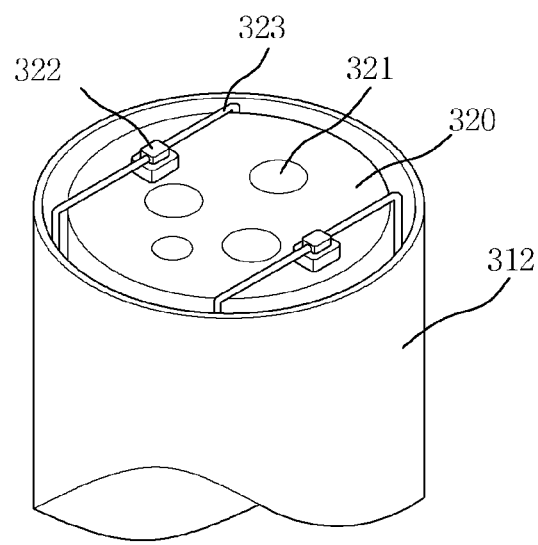
FIG. 9 is a perspective view of a coupled structure of a fixture and a rotating frame.
Figure 10:
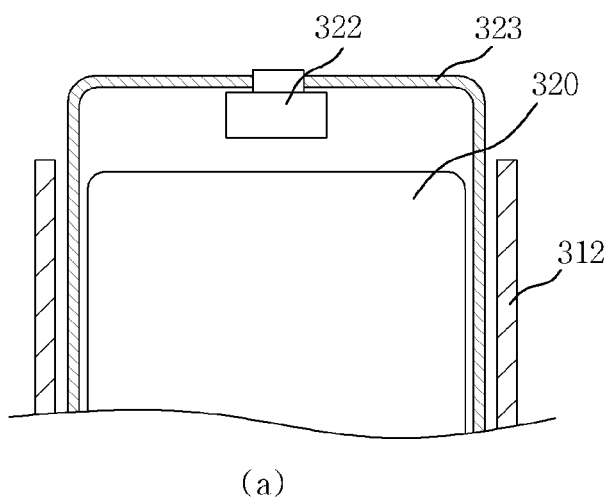
FIG. 10 is an operation state diagram of the fixture of FIG. 9.
Figure 10:
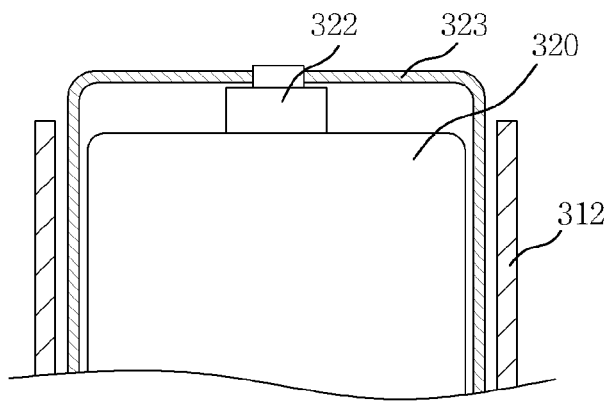
Figure 11:
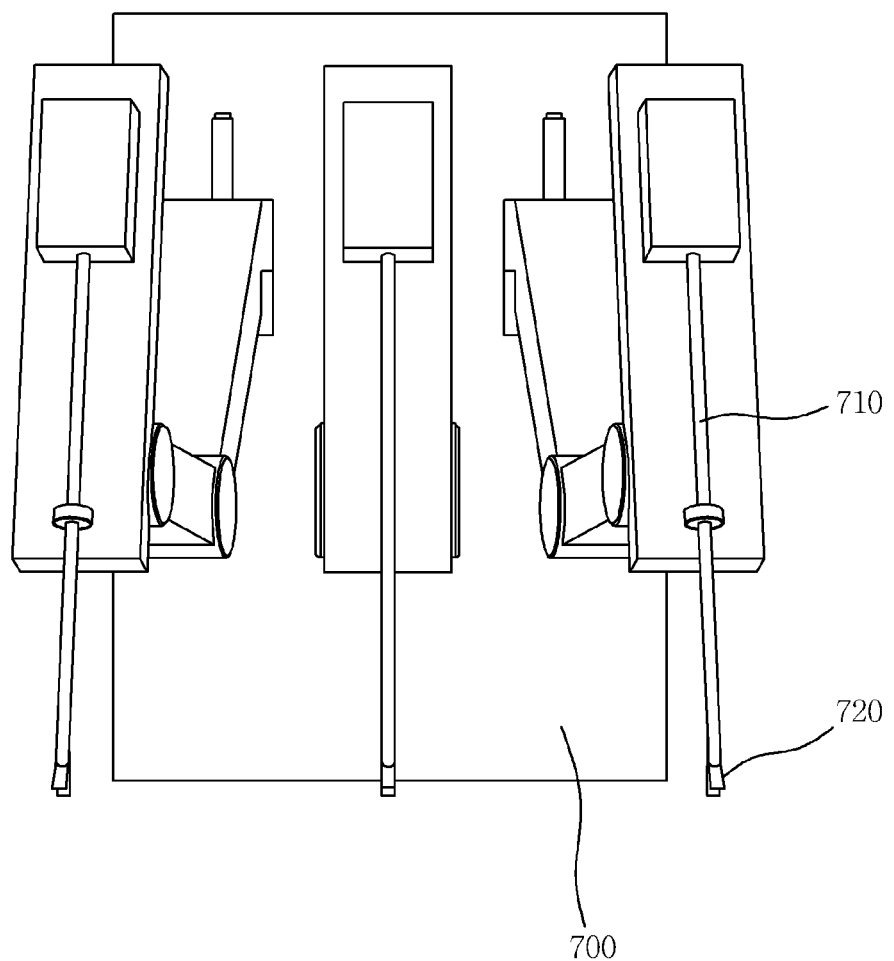
FIG. 11 is a schematic diagram of a surgical robot according to the related art.

FIG. 9 is a perspective view of a coupled structure of a fixture and the rotating frame 320 and FIG. 10 is a diagram illustrating an operation state of the fixture of FIG. 9. The rotating frame 320 may be coupled with the fixture capable of selecting an unlocking/locking state by pulling a fixed plate 322 by a tension wire 323 so as to rotate the surgical equipment 500 to a desired position and then fix the surgical equipment 500. FIG. 10A illustrates the unlocking state of the fixture and FIG. 10B illustrates the locking state of the fixture.

By the above configuration, when the surgical robot for changing a position of surgical equipment according to the embodiment of the present invention allows the rotating driving part 240 to rotate the rotating plate 211 or rotates the housing front end 210, the spacer 340, the rotating link 330, the rotating frame 320, and the surgical equipment 500 rotate integrally through the plurality of flexible shafts 410, thereby easily changing the position of the surgical equipment at narrow affected areas without detaching and attaching the surgical equipment.

Hereinafter, a use method of the surgical robot for changing a position of surgical equipment according to the embodiment of the present invention will be described with reference to the surgery of the occipital region, by way of example.

A patient lays down on an operation table, opening his/her mouth and an operator grips the holding member 600 at a patient's bedside and inserts the curved part 312 of the curved frame 300 into a patient's oral cavity or inserts the curved part 312 of the curved frame into a patient's oral cavity by electronically controlling the surgical robot for changing a position of surgical equipment according to the embodiment of the present invention. That is, this state is a state in which the curved part 312 of the curved frame and the rotating frame 320 are positioned at an oral cavity and an occipital region and the straight part 311 and the housing 200 of the curved frame and the holding member 600 are disposed on a patient's nose, brow, and forehead.

In this state, an operator figures out a position to be operated by looking at an image captured by an endoscope installed in the curved part 312 through a display and appropriately manipulates a control interface to operate the rotating driving part 240 so as to dispose the required surgical equipments 500 in the vicinity of the surgical site or manually rotates the housing front end 210 to rotate the flexible shaft 410 and then may perform the surgery using the surgical equipments in the state in which the corresponding flexible shaft 410 is translated, rotated, or bent.

As such, the surgical robot for changing a position of surgical equipment according to the embodiment of the present invention may appropriately change the position of the surgical equipment to various positions in the state in which the surgical robot is disposed in the narrow affected areas, without performing the operation of inserting or extracting the surgical robot into or from the affected areas.

DETAILED DESCRIPTION OF MAIN ELEMENTS

100 Frame fixing part
200 housing
210 housing front end
211 rotating plate
212, 222 saw-toothed projection
213 screw shaft
214 coupling member
215 fixing hole
216 moving member
217 straight moving member
220 housing rear end
223 spring
224 washer
225 nut
226 through hole 227 fixing pin
230 shaft holder
240 rotating driving part
250 operation driving part
300 curved frame
310 fixed frame
311 straight part
312 cured part
320 rotating frame
321 channel
330 rotating link
340 spacer
350 member elastically deformed in longitudinal direction
400 shaft assembly
410 flexible shaft
500 surgical equipment
600 holding member
POW power terminal
CON control terminal

The invention claimed is:

1. A surgical robot for changing a position of surgical equipment, comprising:
a frame fixing part;
a housing coupled with a rear end of the frame fixing part;
a curved frame coupled with a leading end of the frame fixing part; and
a shaft assembly,
wherein the shaft assembly passes through the curved frame to be exposed to a leading end of the curved frame, continues into the housing, and rotates within the curved frame,
wherein the shaft assembly includes a plurality of flexible shafts having surgical equipments, and each of the surgical equipments is attached to a leading end of each of the plurality of flexible shafts,
wherein the curved frame includes a fixed frame coupled with the leading end of the frame fixing part, and a rotating frame rotatably mounted at a leading end of the fixed frame, and
wherein the rotating frame is formed with a channel through which the plurality of flexible shafts slides.

2. The surgical robot of claim 1, wherein the housing includes a housing rear end and a housing front end coupled with the shaft assembly, and the housing front end rotates with respect to the housing rear end.

3. The surgical robot of claim 1, wherein a leading end of the housing is provided with a rotating plate rotating by a rotating driving part, and the rotating plate is coupled with a shaft holder into which the plurality of flexible shafts is inserted.

4. The surgical robot of claim 3, wherein the shaft holder is detachably coupled with a moving member within the housing to advance and retreat the plurality of flexible shafts.

5. The surgical robot of claim 4, wherein each surface on which the shaft holder and the moving member coupled with each other is formed with power terminals and control terminals.

6. The surgical robot of claim 1, wherein the fixed frame includes a straight part fixed to the frame fixing part and a curved part connected to a leading end of the straight part, and the straight part and the curved part are a rigid body.

7. The surgical robot of claim 6, wherein the curved part has one or more rotating links embedded therein, the one or more rotating links being formed with through holes through which the plurality of flexible shafts penetrates, and the one or more rotating links rotate together when the plurality of flexible shafts rotates.

8. The surgical robot of claim 7, wherein the straight part has a spacer maintaining an interval between the plurality of flexible shafts embedded therein and the spacer rotates together when the plurality of flexible shafts rotates.

9. The surgical robot of claim 8, wherein the rotating frame, the one or more rotating links, and the spacer are connected to each other by a member elastically deformed in a longitudinal direction.

10. The surgical robot of claim 1, wherein the rotating frame is coupled with a fixture configured to include a fixed plate and a tension wire the fixed plate.

11. The surgical robot of claim 1, wherein the plurality of flexible shafts includes a flexible shaft having forceps attached to a leading end thereof and a flexible shaft having scissors attached to a leading end thereof.

12. The surgical robot of claim 11, wherein the plurality of flexible shafts further includes a flexible shaft having accessory devices attached to a leading end thereof.

* * * * *